United States Patent
Nord et al.

(10) Patent No.: US 12,252,594 B2
(45) Date of Patent: Mar. 18, 2025

(54) METHOD OF PREPARING A HYDROGEL PRODUCT

(71) Applicant: GALDERMA HOLDING SA, La Tour-De-Peilz (CH)

(72) Inventors: Lars Nord, Uppsala (SE); Hotan Mojarradi, Uppsala (SE); Johan Olsson, Bromma (SE)

(73) Assignee: Galderma Holding SA, Zug (CH)

( * ) Notice: Subject to any disclaimer, the term of this patent is extended or adjusted under 35 U.S.C. 154(b) by 1357 days.

(21) Appl. No.: 16/729,179

(22) Filed: Dec. 27, 2019

(65) Prior Publication Data

US 2020/0140626 A1 May 7, 2020

Related U.S. Application Data

(63) Continuation of application No. PCT/EP2018/067257, filed on Jun. 27, 2018.

(30) Foreign Application Priority Data

Jun. 28, 2017 (EP) .................................... 17178474
Jun. 28, 2017 (EP) .................................... 17178479

(51) Int. Cl.
*C08J 3/075* (2006.01)
*C08J 3/24* (2006.01)
*C08K 5/1545* (2006.01)

(52) U.S. Cl.
CPC ............... *C08J 3/075* (2013.01); *C08J 3/24* (2013.01); *C08J 2305/02* (2013.01); *C08J 2305/10* (2013.01); *C08K 5/1545* (2013.01)

(58) Field of Classification Search
CPC . C08J 3/075; C08J 3/24; C08J 2305/02; C08J 2305/10; C08J 2305/08; C08K 5/1545; A61Q 19/00; C08B 37/0012; C08B 37/0021; C08B 37/0063; C08B 37/0072; C08L 5/08; A61K 8/735
See application file for complete search history.

(56) References Cited

U.S. PATENT DOCUMENTS

| 2018/0244807 A1* | 8/2018 | Karlsson ................. A61P 17/00 |
| 2019/0023812 A1* | 1/2019 | Mojarradi ................ A61K 8/73 |

FOREIGN PATENT DOCUMENTS

| WO | WO-00/46252 A1 | 8/2000 |
| WO | WO-2015/181366 A1 | 12/2015 |
| WO | WO-2016/107834 A1 | 7/2016 |
| WO | WO-2016/192760 A1 | 12/2016 |

OTHER PUBLICATIONS

International Search Report and Written Opinion issued in International Application No. PCT/EP2018/067257, mailed on Sep. 26, 2018.

* cited by examiner

Primary Examiner — Robert S Jones, Jr.
Assistant Examiner — Jiangtian Xu
(74) Attorney, Agent, or Firm — Foley & Lardner LLP; Sunit Talapatra

(57) ABSTRACT

A method of preparing a hydrogel product comprising crosslinked glycosaminoglycan molecules, comprising the steps of: (a) providing a mixed solution of glycosaminoglycan molecules, a di- or multinucleophilic functional crosslinker, and a mononucleophilic functional graft chain; (b) activating carboxyl groups on the glycosaminoglycan molecules with a coupling agent to form activated glycosaminoglycan molecules; and (c) simultaneously crosslinking the activated glycosaminoglycan molecules and grafting the graft chain to the activated glycosaminoglycan molecules by reacting the nucleophiles with the activated carboxyl groups.

29 Claims, No Drawings

METHOD OF PREPARING A HYDROGEL PRODUCT

CROSS-REFERENCE TO RELATED APPLICATIONS

The present application is a Continuation of International Patent Application No. PCT/EP2018/067257, filed Jun. 27, 2018, and claims the benefit of priority to European Patent Application No. 17178474.7, filed Jun. 28, 2017, and European Patent Application No. 17178479.6, filed Jun. 28, 2017, the entire contents of which are hereby incorporated by reference.

TECHNICAL FIELD

The present invention relates to the field of hydrogels containing cross-linked polysaccharides and the use of such hydrogels in medical and/or cosmetic applications. More specifically, the present invention is concerned with methods for preparing crosslinked and modified polysaccharides.

BACKGROUND OF THE INVENTION

One of the most widely used biocompatible polymers for medical use is hyaluronic acid (HA). It is a naturally occurring polysaccharide belonging to the group of glycosaminoglycans (GAGs). Hyaluronic acid and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

Water-absorbing gels, or hydrogels, are widely used in the biomedical field. They are generally prepared by chemical cross-linking of polymers to infinite networks. While native hyaluronic acid and certain cross-linked hyaluronic acid products absorb water until they are completely dissolved, cross-linked hyaluronic acid gels typically absorb a certain amount of water until they are saturated, i.e. they have a finite liquid retention capacity, or swelling degree.

Since hyaluronic acid is present with identical chemical structure except for its molecular mass in most living organisms, it gives a minimum of reactions and allows for advanced medical uses. Cross-linking and/or other modifications of the hyaluronic acid molecule is necessary to improve its duration in vivo. Furthermore, such modifications affect the liquid retention capacity of the hyaluronic acid molecule. As a consequence thereof, hyaluronic acid has been the subject of many modification attempts.

Another widely used biocompatible polymer is dextran. Dextran is a complex, branched glucan composed of chains of varying lengths (from 1 to 2000 kD). The straight chain consists of $\alpha$-1,6 glycosidic linkages between glucose molecules, while branches begin from $\alpha$-1,3 linkages.

Cyclodextrins (sometimes called cycloamyloses), also referred to herein as CDs, are a family of compounds made up of sugar molecules bound together in a ring (cyclic oligosaccharides). Cyclodextrins are produced from starch by means of enzymatic conversion. Typically, cyclodextrins are constituted by 6-8 glucopyranoside units, and have a structural conformation resembling toroids with the primary hydroxyl groups of the glucopyranoside units arranged along the smaller opening of the toroid and the secondary hydroxyl groups of the glucopyranoside units arranged along the larger opening of the toroid. Because of this arrangement, the interior of the toroids is considerably less hydrophilic than the aqueous environment and thus able to host other hydrophobic molecules. In contrast, the exterior is sufficiently hydrophilic to impart cyclodextrins (or their complexes) water solubility.

When a hydrophobic molecule (the guest) is contained, fully or partially, within the interior of the cyclodextrin (the host), this is referred to as an inclusion complex or guest/host complex. The formation of the guest/host complex can greatly modify the physical and chemical properties of the guest molecule, mostly in terms of water solubility. This is a reason why cyclodextrins have attracted much interest in pharmaceutical applications: because inclusion compounds of cyclodextrins with hydrophobic molecules are able to penetrate body tissues, these can be used to release biologically active compounds under specific conditions. In most cases the mechanism of controlled degradation of such complexes is based on change of pH, leading to the cleavage of hydrogen or ionic bonds between the host and the guest molecules. Other mechanisms for the disruption of the complexes include heating or action of enzymes able to cleave $\alpha$-1,4 linkages between glucose monomers.

SUMMARY OF THE INVENTION

It is an object of the present invention to provide a cross-linked hyaluronic acid product suitable for use as a dermal filler.

It is a further object of the present invention to provide a cross-linked hyaluronic acid product suitable having improved durability in use as a dermal filler.

It is a further object of the present invention to provide a cross-linked hyaluronic acid product suitable having desired swelling.

It is a further object of the present invention to provide a cross-linked Hyaluronic acid product that treat skin aging by promoting collagen neosynthesis in the skin.

It is a further object of the present invention to provide improved formulations for administration of pharmaceutical and/or cosmetic substances.

In particular, it is an object of the present invention to provide a stable cross-linked hyaluronic acid gel product having a significant amount of grafted cyclodextrins.

It is also an object of the present invention to provide a method for preparing improved formulations for administration of pharmaceutical and/or cosmetic substances.

In particular, it is an object of the present invention to a method for providing a stable cross-linked hyaluronic acid gel product having a significant amount of grafted cyclodextrins.

For these and other objects that will be evident from this disclosure, the present invention provides according to a first aspect a method of preparing a hydrogel product comprising crosslinked glycosaminoglycan molecules, comprising the steps of:

(a) providing a mixed solution of glycosaminoglycan molecules, a di- or multinucleophilic functional crosslinker, and a mononucleophilic functional graft chain;

(b) activating carboxyl groups on the glycosaminoglycan molecules with a coupling agent to form activated glycosaminoglycan molecules;

(c) simultaneously crosslinking the activated glycosaminoglycan molecules and grafting the graft chain to the activated glycosaminoglycan molecules by reacting the nucleophiles with the activated carboxyl groups.

Cross-linking and/or other modifications of glycosaminoglycan molecules, for example hyaluronic acid, is necessary to improve its duration in vivo. The present invention provides a simple one-pot/one-step manufacturing method for preparing crosslinked and grafted glycosaminoglycan molecules. The one-pot/one-step manufacturing method reduces the number of steps in the process of manufacturing crosslinked and grafted glycosaminoglycan. The one-pot/one-step method according to the present disclosure is thus a more simple method compared to e.g. a two-step cross-linking and grafting process. The process thereby saves time and money. However, since the processing and modification of glycosaminoglycan molecules, and particularly hyaluronic acid, typically leads to a certain degree of degradation of the polymer backbone, reducing the number of processing and modification steps may also result in an improved, less degraded glycosaminoglycan product.

The term cross-linking as used herein refers to a reaction involving sites or groups on existing macromolecules or an interaction between existing macromolecules that results in the formation of a small region in a macromolecule from which at least four chains emanate. A reaction of a reactive chain end of a linear macromolecule with an internal reactive site of another linear macromolecule results in the formation of a branch point or graft, but is not regarded as a cross-linking reaction.

The term grafting as used herein refers to a reaction in which one or more species are connected to the main chain of a macromolecule as side-chains having constitutional or configurational features that differ from those in the main chain.

The composition formed using the inventive method is a hydrogel. That is, it can be regarded as a water-insoluble, but substantially dilute crosslinked system of glycosaminoglycan molecules when subjected to a liquid, typically an aqueous liquid.

The hydrogel composition contains mostly liquid by weight and can e.g. contain 90-99.9% water, but it behaves like a solid due to a three-dimensional crosslinked hyaluronic acid network within the liquid. Due to its significant liquid content, the gel is structurally flexible and similar to natural tissue, which makes it very useful as a scaffold in tissue engineering and for tissue augmentation.

The hydrogel composition is preferably biocompatible. This implies that no, or only very mild, immune response occurs in the treated individual. That is, no or only very mild undesirable local or systemic effects occur in the treated individual.

According to a preferred embodiment, the cross-linked hydrogel product is in the form of gel particles having an average size in the range of 0.01-5 mm, preferably 0.1-0.8 mm.

In some embodiments, the glycosaminoglycan molecules are selected from the group consisting of hyaluronic acid, chondroitin and chondroitin sulfate, and mixtures thereof. In some embodiments, the glycosaminoglycan molecules are hyaluronic acid.

Unless otherwise provided, the term "hyaluronic acid" encompasses all variants and combinations of variants of hyaluronic acid, hyaluronate or hyaluronan, of various chain lengths and charge states, as well as with various chemical modifications, including crosslinking. That is, the term also encompasses the various hyaluronate salts of hyaluronic acid with various counter ions, such as sodium hyaluronate. Various modifications of the hyaluronic acid are also encompassed by the term, such as oxidation, e.g. oxidation of —CH$_2$OH groups to —CHO and/or —COOH; periodate oxidation of vicinal hydroxyl groups, optionally followed by reduction, e.g. reduction of —CHO to —CH$_2$OH or coupling with amines to form imines followed by reduction to secondary amines; sulphation; deamidation, optionally followed by deamination or amide formation with new acids; esterification; crosslinking; substitutions with various compounds, e.g. using a crosslinking agent or a carbodiimide assisted coupling; including coupling of different molecules, such as proteins, peptides and active drug components, to hyaluronic acid; and deacetylation. Other examples of modifications are isourea, hydrazide, bromocyan, monoepoxide and monosulfone couplings.

The hyaluronic acid can be obtained from various sources of animal and non-animal origin. Sources of non-animal origin include yeast and preferably bacteria. The molecular weight of a single hyaluronic acid molecule is typically in the range of 0.1-10 MDa, but other molecular weights are possible.

In certain embodiments the concentration of the glycosaminoglycan is in the range of 1 to 100 mg/ml. In some embodiments the concentration of the glycosaminoglycan is in the range of 2 to 50 mg/ml. In specific embodiments the concentration of the glycosaminoglycan is in the range of 5 to 30 mg/ml or in the range of 10 to 30 mg/ml.

Crosslinking of the glycosaminoglycan can be achieved by modification with a crosslinking agent. In preferred embodiments, crosslinking of the glycosaminoglycan is achieved by amide coupling of glycosaminoglycan molecules. Amide coupling using a using a di- or multinucleophilic functional crosslinker together with a coupling agent is an attractive route to preparing crosslinked glycosaminoglycan molecules useful for hydrogel products. Crosslinking can be achieved using a non-carbohydrate based di- or multinucleophilic crosslinker, for example hexamethylenediamine (NMDA), or a carbohydrate based di- or multinucleophilic crosslinker, for example diaminotrehalose (DATH) together with a glycosaminoglycan. Crosslinking can also be achieved using an at least partially deacetylated glycosaminoglycan, either alone or in combination with a second glycosaminoglycan, whereby the deacetylated glycosaminoglycan itself acts as the di- or multinucleophilic crosslinker.

Crosslinking of the glycosaminoglycan may for example be achieved in aqueous media using a crosslinker comprising at least two nucleophilic functional groups, for example amine groups, capable of forming covalent bonds directly with carboxylic acid groups of GAG molecules by a reaction involving the use of a coupling agent.

The crosslinker comprising at least two nucleophilic functional groups may for example be a non-carbohydrate based di- or multinucleophilic crosslinker or a carbohydrate based di- or multinucleophilic crosslinker.

Carbohydrate based di- or multinucleophilic crosslinkers are preferred, since they provide a hydrogel product based entirely on carbohydrate type structures or derivatives thereof, which minimizes the disturbance of the crosslinking on the native properties of the glycosaminoglycans. The crosslinker itself can also contribute to maintained or increased properties of the hydrogel, for example when crosslinking with a structure that correlates to hyaluronic acid or when crosslinking with a structure with high water retention properties.

The carbohydrate based di- or multinucleophilic crosslinker may for example be selected from the group consisting of di- or multinucleophilic functional di-, tri-, tetra-, oligosaccharides, and polysaccharides.

In some embodiments, the crosslinks comprise a spacer group selected from the group consisting of di-, tri-, tetra-, and oligosaccharides.

In some embodiments, the spacer group is a hyaluronic acid tetrasaccharide, hyaluronic acid hexasaccharide, trehalose, lactose, maltose, sucrose, cellobiose or raffinose residue.

In some embodiments, the spacer group is selected from the group consisting of di-, tri-, and tetrasaccharides.

In some embodiments, the nucleophilic groups of the crosslinker are selected from the group consisting of primary amine, hydrazine, hydrazide, carbazate, semi-carbazide, thiosemicarbazide, thiocarbazate and aminoxy. In preferred embodiments, the nucleophilic groups of the crosslinker are primary amine.

In some embodiments, the crosslinker is a dinucleophilic functional crosslinker.

In some embodiments, the crosslinker is selected from the group consisting of diamino hyaluronic acid tetrasaccharide, diamino hyaluronic acid hexasaccharide, diamino trehalose, diamino lactose, diamino maltose, diamino sucrose, chitobiose, or diamino raffinose. In a preferred embodiment, the crosslinker is diamino trehalose (DATH).

Diaminotrehalose (DATH) can be synthesized as described in "*Synthetic Carbohydrate Polymers Containing Trehalose Residues in the Main Chain: Preparation and Characteristic Properties*"; Keisuke Kurita, *Naoko Masuda, Sadafumi Aibe, Kaori Murakami, Shigeru Ishii, and Shin-Ichiro Nishimurat; *Macromolecules* 1994, 27, 7544-7549.

In a preferred embodiment, the di- or multinucleophilic crosslinker is an at least partially deacetylated glycosaminoglycan, i.e. an acetylated glycosaminoglycan which has been at least partially deacetylated to provide a glycosaminoglycan having free amine groups. An at least partially deacetylated glycosaminoglycan, can be crosslinked either alone or in combination with a second glycosaminoglycan, whereby the deacetylated glycosaminoglycan itself acts as the di- or multinucleophilic crosslinker.

According to some embodiments, the at least partially deacetylated glycosaminoglycan is selected from the group consisting of deacetylated hyaluronic acid, deacetylated chondroitin and deacetylated chondroitin sulfate, and mixtures thereof. According to some embodiments, the at least partially deacetylated glycosaminoglycan is deacetylated hyaluronic acid.

According to some embodiments, the at least partially deacetylated glycosaminoglycan has a degree of acetylation of 99% or less, preferably 98% or less, preferably 97% or less, preferably 96% or less, preferably 95% or less, preferably 94% or less, preferably 93% or less, and a weight average molecular weight of 0.1 MDa or more, preferably 0.5 MDa or more.

According to some embodiments, the at least partially deacetylated glycosaminoglycan is obtained by a method for at least partial deacetylation of a glycosaminoglycan, comprising:
 a1) providing a glycosaminoglycan comprising acetyl groups;
 a2) allowing the glycosaminoglycan comprising acetyl groups to react with hydroxylamine ($NH_2OH$) or a salt thereof at a temperature of 100° C. or less for 2-200 hours to form an at least partially deacetylated glycosaminoglycan; and
 a3) recovering the at least partially deacetylated glycosaminoglycan.

According to some embodiments, the second glycosaminoglycan is selected from the group consisting of hyaluronic acid, chondroitin and chondroitin sulfate, and mixtures thereof. According to some embodiments, the second glycosaminoglycan is hyaluronic acid.

In some embodiments, the crosslinking and grafting of step (c) provides amide bonds between glycosaminoglycan molecules and crosslinkers and between glycosaminoglycan molecules and graft chains. Amide bonds are stable covalent bonds that are not easily hydrolysed. Accordingly, hydrogel products according to the invention, where both crosslinking and grafting is effected by amide bonds will be less sensitive to degradation than similar products where crosslinking or grafting is effected by a weaker bond. Using the same types of bond in crosslinking and grafting may also provide a more predictable degradation behaviour of the product.

In some embodiments, the mononucleophilic functional graft chain is a mononucleophilic functional carbohydrate.

In some embodiments, the mononucleophilic functional graft chain is an aminodextran and/or an aminocyclodextrin.

In some embodiments, the molar ratio of the aminodextran and/or aminocyclodextrin to the disaccharides of the glycosaminoglycan is 0.1-50%, preferably 1-20% and more preferably 8-12%.

In some embodiments, the aminodextran and/or aminocyclodextrin contain a linking group having an amino group, wherein the linking group of the aminodextran and/or aminocyclodextrin forms an amide bond with a carboxyl group of the glycosaminoglycan.

In some embodiments, the linking group contains a C1-6 alkyl. In some embodiments, the linking group contains a C1-4 alkyl.

Unless otherwise provided, the term "dextran" encompasses all variants and combinations of variants of dextran, of various chain lengths and charge states, as well as with various chemical modifications. Dextran is a complex, branched glucan composed of chains of varying lengths (from 1 to 2000 kD). The straight chain consists of $\alpha$-1,6 glycosidic linkages between glucose molecules, while branches begin from $\alpha$-1,3 linkages. Dextran is a bacterial polysaccharide and may be synthesized from sucrose by certain lactic-acid bacteria, for example, *Leuconostoc mesenteroides* and *Streptococcus mutans*. Dextran is a nontoxic polysaccharide, for which biocompatibility has been well documented. Dextran has been extensively explored in biomedical and pharmaceutical applications. Dextrans are commonly used to decrease vascular thrombosis, reduce inflammatory response and prevent ischemia reperfusion injury in organ transplantation, in which dextran acts as a mild reactive oxygen species scavenger and reduces excess platelet activation.

In some embodiments, the aminodextran and/or aminocyclodextrin is an aminodextran. In some embodiments, the aminodextran has an average molecular weight of less than 10 kDa. In some embodiments, the aminodextran has an average molecular weight of less than 5 kDa.

In some embodiments, the aminodextran and/or aminocyclodextrin is covalently grafted to the activated glycosaminoglycan by single end-point attachment.

In some embodiments, the aminodextran is functionalized at the reducing end with a diamine.

In some embodiments, the aminodextran and/or aminocyclodextrin is an aminocyclodextrin. In some embodiments, the aminocyclodextrin is constituted by 5-32 glucopyranoside units. In some embodiments, the aminocyclodextrin is constituted by 6-8 glucopyranoside units. In some embodiments, the aminocyclodextrin is constituted by 6 glucopyranoside units ($\alpha$-cyclodextrin). In some embodiments, the aminocyclodextrin is constituted by 7 glucopyranoside units ($\beta$-cyclodextrin). In some embodiments, the aminocyclodextrin is constituted by 8 glucopyranoside units (γ-cyclodextrin).

In some embodiments, the aminocyclodextrin is selected from the group consisting of 2-aminocyclodextrin, 3-aminocyclodextrin and 6-aminocyclodextrin. In some embodiments, the aminocyclodextrin is selected from the group consisting of 3-aminocyclodextrin and 6-aminocyclodextrin. In some embodiments, the aminocyclodextrin is 6-aminocyclodextrin.

According to some embodiments, the hydrogel product is further comprising a guest molecule capable of forming a guest-host complex with the cyclodextrin molecule acting as a host. The guest molecule may be selected from drugs and/or biologically active substances used in the treatment of disorders in the field of dermatology, aesthetics, ophthalmology, gynecology, oncology, angiology, neurology, orthopaedics, rheumatology or aesthetic dermatology.

In some embodiments, at least 90% of the bonds between glycosaminoglycan molecules and crosslinks and between glycosaminoglycan molecules and graft chains are amide bonds.

In some embodiments, less than 5% of the bonds between glycosaminoglycan molecules and crosslinks and between glycosaminoglycan molecules and graft chains are ester bonds.

The coupling agent may for example be selected from the group consisting of triazine-based coupling agents, carbodiimide coupling agents, imidazolium-derived coupling reagents, Oxyma and COMU. A preferred coupling agent is a triazine-based coupling agent, including the group consisting of 4-(4,6-dimethoxy-1,3,5-triazin-2-yl)-4-methylmorpholinium chloride (DMTMM) and 2-chloro-4,6-dimethoxy-1,3,5-triazine (CDMT). In preferred embodiments, the coupling agent is DMTMM.

When a hyaluronic acid gel is grafted with dextran, it has unexpectedly been found that the molar ratio between DMTMM and the disaccharide repeating units of the hyaluronic acid affects the swelling of the grafted gel. Specifically, gels with the same concentration of grafted dextran will exhibit lower swelling when the grafting has been done with a higher DMTMM/disaccharide repeating unit ratio. Accordingly, the swelling of the gel product can be controlled by variation of the amount of DMTMM used.

In some embodiments, the DMTMM/disaccharide repeating unit ratio is in the range of 1-10. In some embodiments, the DMTMM/disaccharide repeating unit ratio is in the range of 1-3. In some embodiments, the DMTMM/disaccharide repeating unit ratio is in the range of 1-1.5. In some embodiments, the DMTMM/disaccharide repeating unit ratio is in the range of 3-10. In some embodiments, the DMTMM/disaccharide repeating unit ratio is in the range of 3-8. In some embodiments, the DMTMM/disaccharide repeating unit ratio is in the range of 4-6.

In some embodiments the glycosaminoglycan is hyaluronic acid and the mononucleophilic functional graft chain is an aminodextran. Hyaluronic acid products obtained according to the present invention, comprising a cross-linked hyaluronic acid with one or more dextran molecules grafted, display several advantageous and surprising properties, e.g. including improved stability to thermal, hydrolytic, radical and enzymatic degradation resulting in improved durability in use as a dermal filler, and decreased swelling capacity. Reduced swelling capacity means that harder gels can be produced, without increasing the amount of cross-linker in the hyaluronic acid.

The cross-linked hyaluronic acid products obtained according to the invention can be used, e.g., as injectable compositions for cosmetic or medical surgery, like dermal filling and body contouring. The cross-linked hyaluronic acid products obtained according to the invention, combining hyaluronic acid with dextran, exhibit decreased swelling compared to hyaluronic acid products without dextran. This is useful, since it means that harder gels can be produced, without increasing the amount of cross-linker in the hyaluronic acid. The cross-linked hyaluronic acid products obtained according to the invention have also been found to have a better thermal stability as well as better stability to radical and enzymatic degradation as compared hyaluronic acid products without dextran. A possible explanation is that the hyaluronic acid backbone is protected by the dextran. This leads to an improved durability in vivo of the cross-linked hyaluronic acid products according to the invention as compared hyaluronic acid products without dextran. In addition to improved stability, the cross-linked hyaluronic acid products obtained according to the invention combining hyaluronic acid with dextran, have been shown to promote collagen neosynthesis.

In some embodiments the glycosaminoglycan is hyaluronic acid and the mononucleophilic functional graft chain is amino functionalized cyclodextrin. This allows for a significant modification of the cross-linked hyaluronic acid with cyclodextrins without inducing depolymerisation of the cross-linked polymer mixture.

The cyclodextrin molecules are useful as carriers (hosts) for a pharmaceutical agent (guest). When a pharmaceutical agent (the guest) is contained, fully or partially, within the interior of the cyclodextrin (the host), this is referred to as an inclusion complex or guest/host complex. The cyclodextrin may then release the pharmaceutical agent under specific conditions, e.g. due to change in pH leading to the cleavage of hydrogen or ionic bonds between the host and the guest molecules.

The cyclodextrin molecules are attached to the cross-linked polymer mixture, preferably to the hyaluronic acid component, in order to reduce migration of the cyclodextrin (or guest/host complex) from the site of administration, e.g. injection. In this way, the site of release of the pharmaceutical agent from the cyclodextrin can be controlled.

Also, in order to increase temporal control of the release of the pharmaceutical agent, it has been found that the influence of cleavage of the bonds between the cyclodextrin (or guest/host complex) and the cross-linked polymer mixture should be minimized. In other words, it is desired that the release of the pharmaceutical agent is, as far as possible dependent on the physical release from the cyclodextrin rather than on chemical degradation.

In preferred hydrogel products, the cyclodextrin molecules are attached to the hyaluronic acid by amide bonds. The use of amide bonds in the cyclodextrin-hyaluronic acid linkage (graft) has been found to be advantageous compared to e.g. ester bonds, since the amide bond is more stable to degradation in vivo. The use of a less stable bond between the hyaluronic acid and cyclodextrin molecules could lead to premature loss of cyclodextrin (or guest/host complex) from the site of injection.

The hydrogel product may further comprise a therapeutically relevant concentration of a local anesthetic. A local anesthetic is a drug that causes reversible local anesthesia and a loss of nociception. When it is used on specific nerve pathways (nerve block), effects such as analgesia (loss of pain sensation) and paralysis (loss of muscle power) can be achieved. The local anesthetic may be added to the composition to reduce pain or discomfort experienced by the patient due to the injection procedure.

According to certain embodiments the local anesthetic is selected from the group consisting of amide and ester type local anesthetics, for example bupivacaine, butanilicaine, carticaine, cinchocaine (dibucaine), clibucaine, ethyl para-piperidinoacetylaminobenzoate, etidocaine, lignocaine (lidocaine), mepivacaine, oxethazaine, prilocaine, ropivacaine, tolycaine, trimecaine, vadocaine, articaine, levobupivacaine, amylocaine, cocaine, propanocaine, clormecaine, cyclomethycaine, proxymetacaine, amethocaine (tetracaine), benzocaine, butacaine, butoxycaine, butyl aminobenzoate, chloroprocaine, dimethocaine (larocaine), oxybuprocaine, piperocaine, parethoxycaine, procaine (novocaine), propoxycaine, tricaine or a combination thereof. According to some preferred embodiments the local anesthetic is lidocaine.

According to specific embodiments the local anesthetic is lidocaine. Lidocaine is a well-known substance, which has been used extensively as a local anesthetic in injectable formulations, such as hyaluronic acid compositions.

The concentration of the amide or ester local anesthetic may be selected by the skilled person within the therapeutically relevant concentration ranges of each specific local anesthetic or a combination thereof. In some embodiments the concentration of said local anesthetic is in the range of 0.1 to 30 mg/ml. In certain embodiments the concentration of said local anesthetic is in the range of 0.5 to 10 mg/ml.

When lidocaine is used as the local anesthetic, the lidocaine may preferably be present in a concentration in the range of 1 to 5 mg/ml, more preferably in the range of 2 to 4 mg/ml, such as in a concentration of about 3 mg/ml.

The method described herein may further involve sterilization of the hydrogel product by autoclaving, i.e sterilization using saturated steam. Accordingly, in some embodiments the hydrogel product has been subjected to sterilization by autoclaving. The autoclaving may be performed at an $F_0$-value >4. The autoclaving may preferably be performed at an $F_0$-value in the range of 10 to 50. The $F_0$ value of a saturated steam sterilisation process is the lethality expressed in terms of the equivalent time in minutes at a temperature of 121° C. delivered by the process to the product in its final container with reference to microorganisms possessing a Z-value of 10.

According to a further aspect there is provided a hydrogel product obtainable by the method described above.

The components, features, effects and advantages of the hydrogel product may be further defined as described above with reference to the method of preparing the hydrogel product.

The hydrogel product according to the invention may be provided in the form of a pre-filled syringe, i.e. a syringe that is pre-filled with the injectable hydrogel composition and autoclaved.

The hydrogel product as described herein may advantageously be used for the transport or administration and slow or controlled release of various pharmaceutical or cosmetic substances.

The hydrogel product described herein may be employed in medical as well as non-medical, e.g. purely cosmetic, procedures by injection of the composition into soft tissues of a patient or subject. The compositions have been found useful in, e.g., soft tissue augmentation, for example filling of wrinkles, by hyaluronic acid gel injection. The compositions have also been found useful in a cosmetic treatment, referred to herein as skin revitalization, whereby small quantities of the hyaluronic acid composition are injected into the dermis at a number of injection sites distributed over an area of the skin to be treated, resulting in improved skin tone and skin elasticity. Skin revitalization is a simple procedure and health risks associated with the procedure are very low.

The hydrogel product may be useful, for example in the treatment of various dermatological conditions. Particularly, there is provided an hydrogel product as described above for use in a dermatological treatment selected from the group consisting of wound healing, treatment of dry skin conditions or sun-damaged skin, treatment of hyper pigmentation disorders, treatment and prevention of hair loss, and treatment of conditions that have inflammation as a component of the disease process, such as psoriasis and asteototic eczema. In other words, there is provided hydrogel product as described above for use in the manufacture of a medicament for use in a dermatological treatment selected from the group consisting of wound healing, treatment of dry skin conditions or sun-damaged skin, treatment of hyper pigmentation disorders, treatment and prevention of hair loss, and treatment of conditions that have inflammation as a component of the disease process, such as psoriasis and asteototic eczema.

According to other aspects illustrated herein, there is provided the use of a hydrogel product as described above for cosmetic, non-medical, treatment of a subject by injection of the composition into the skin of the subject. A purpose of the cosmetic, non-medical, treatment may be for improving the appearance of the skin, preventing and/or treating hair loss, filling wrinkles or contouring the face or body of a subject. The cosmetic, nonmedical, use does not involve treatment of any form of disease or medical condition. Examples of improving the appearance of the skin include, but are not limited to, treatment of sun-damaged or aged skin, skin revitalization, skin whitening and treatment of hyper pigmentation disorders such as senile freckles, melasma and ephelides.

Other aspects and preferred embodiments of the present invention will be evident from the following detailed disclosure of the invention and the appended claims. Without desiring to be limited thereto, the present invention will in the following be illustrated by way of examples.

EXAMPLES

Characterization
Reductive Amination on Dextran
The total DEX-HMDA (including mono- and cross-linked HMDA to dextran and free dextran) was determined by $^1$H NMR by comparing the integral of the signals from the anomeric proton of dextran (4.94 ppm), hexamethylenediamine signal (1.33 ppm) and KHP (7.62 ppm, internal standard)
LC-QToF-MS analysis was made to evaluate the residual hexamethylenediamine (HMDA) in the powder after reductive amination.
Amide Crosslinked Hyaluronan Hydrogels with Grafted Dextran
Swelling was done in saline
$MoD_{DEX/diHA}$—"degree of modification" of dextran on hyaluronan is measured with $^1$H NMR. The integral of the anomeric proton of dextran is compared to the integral of the N-acetyl group of hyaluronan. The average number of glucose units in the dextran and thus anomeric protons is 3.7, which the integral is divided with according to the equation below. The hydrogels were degraded with chondroitinase ABC or HCl prior to the analysis.

$$MoD_{DEX/diHA}(\%) = \left( \frac{\frac{\text{Integral of anomeric proton of dextran}}{3.7}}{\frac{\text{Integral of } N\text{-}acetyl \text{ of hyaluronan}}{3}} \right) * 100$$

GelP—"Gel part" is a description of the percentage of polysaccharide that is a part of the gel network. A number of 90% means that only 10% of polysaccharide is not a part the network. The amount of free polysaccharide in the gel was quantified with $^1$H NMR. The hydrogels were degraded with chondroitinase ABC or HCl prior to the analysis.

SwF—Swelling factor analysis was done in saline.

SwCC—"Corrected swelling capacity" is the total liquid uptake of one gram polysaccharide, corrected for gel part.

Mw—The mass average molecular mass

SwC—Swelling capacity in saline, total liquid uptake per gram PS (mL/g).

Diaminotrehalose (DATH) is synthesized as described in "*Synthetic Carbohydrate Polymers Containing Trehalose Residues in the Main Chain: Preparation and Characteristic Properties*"; Keisuke Kurita, *Naoko Masuda, Sadafumi Aibe, Kaori Murakami, Shigeru Ishii, and Shin-Ichiro Nishimurat; *Macromolecules* 1994, 27, 7544-7549.

Example 1—Reductive Amination of Dextran

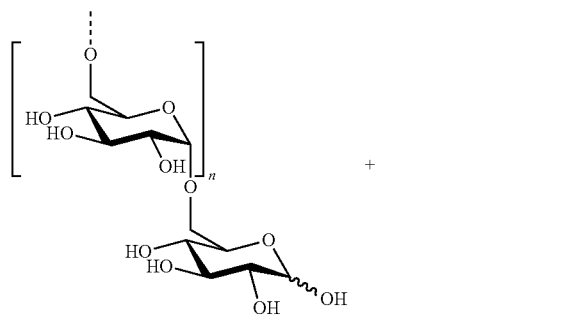

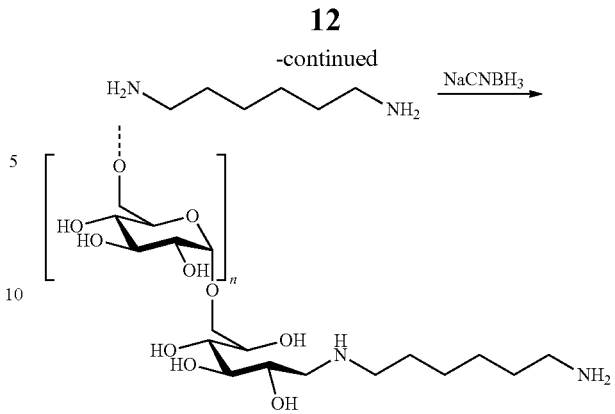

Dextran (100.0 g) with a number average molecular weight ($M_n$) of 849 Da, hexamethylenediamine dihydrochloride (HMDA, 193.3 g) and NaCNBH$_3$ (64.8 g) were added to a reaction vessel. The reagents were dissolved in water (500 g) and the pH was adjusted to pH 10.0 by adding 1 M NaOH. The reaction mixture was incubated at 60° C.

After 4 hours, the reaction was neutralized to pH 7 by adding HCl (aq. 1.2 M) and NaCl (approx. 10 g) was added to facilitate precipitation. The crude reaction was precipitated by slowly addition of the mixture to ethanol under agitation by an over-head stirrer until the final ethanol concentration was 90%. The precipitate was washed with ethanol (90%) numerous times to completely remove residual chemicals and subsequently dried in under vacuum.

The dry powder was dissolved in D$_2$O and analyzed by $^1$H NMR. The total DEX-HMDA content was 75 w/w %. The residual HMDA in the powder was 0.03 w/w %.

Example 2—One-Pot Crosslinking and Drafting of Hyaluronan with Dextran

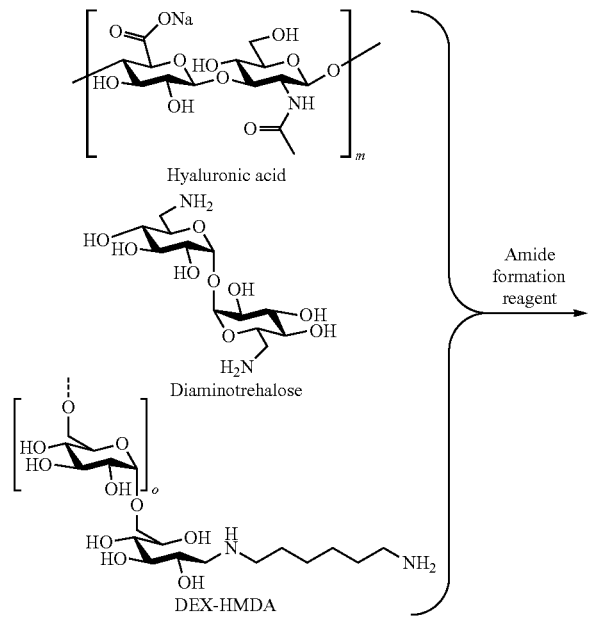

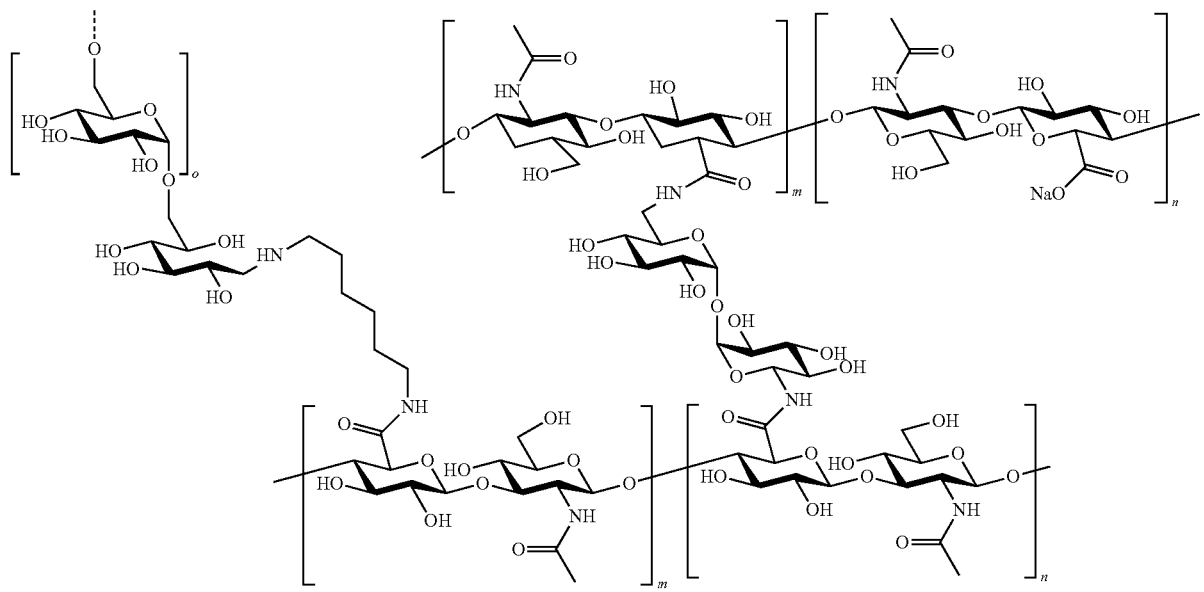

Amide-crosslinked hyaluronic acid with grafted dextran

Hyaluronic acid (HA) was weighed in a reaction vessel. A stock solution of the crosslinker (DATH) was prepared by dissolving it in buffer pH 7. DMTMM and DEX-HMDA were weighed in a PTFE-container and the DATH-solution was added to the DMTMM and DEX-HMDA (for details, see Table 1). The pH of the reagent solution was adjusted to 6-7 with HCl (aq. 1.2 M) and then added to the HA. The mixture was thoroughly homogenized and then incubated at 50° C. for 24 h.

The resulting material was pressed through a 1 mm steel mesh two times and then treated with NaOH solution (pH 13 for 60 min). The gel was neutralized with HCl (aq. 1.2 M) to pH 7 and washed with an excess of sodium chloride solution to remove excess of reagents. The washed gel was precipitated with ethanol. The resulting precipitate was washed with ethanol (70 w/w %) to remove salts and subsequent ethanol to remove water. The obtained powder was dried in under vacuum over night.

The precipitate was swelled in 0.7% NaCl in 8 mM phosphate buffer pH 7.4 and then pressed through a 125 µm filter mesh three times. The gel was filled on syringes and sterilized (125° C., 5.5 min, F0 23). Gel properties is presented in Table 2.

TABLE 1

| | Reaction Conditions | | | | |
|---|---|---|---|---|---|
| Example | HA Start <Mw> (k) | DATH/HA (mol %) | DMTMM/HA (mol %) | DEX-HMDA (mol %) | HA (w/w %) |
| 2-1 | 240 | 0.6 | 125 | 41 | 15.0 |
| 2-2 | 170 | 0.9 | 125 | 41 | 7.5 |
| 2-3 | 170 | 0.6 | 125 | 41 | 7.5 |

TABLE 2

| | Gel Properties | | |
|---|---|---|---|
| Example | MoD (DEX/diHA) (%) | [PS] (mg/mL) | SwF (mL/g) |
| 2-1 | 20% | 62 | 1.9 |
| 2-2 | 17% | 53 | 4.3 |
| 2-3 | 20% | 55 | 4.8 |

Example 3a—Comparative Example, Two Step Process for Manufacturing of Amide Crosslinked Hyaluronan Gels Grafted with Dextran; Step 1
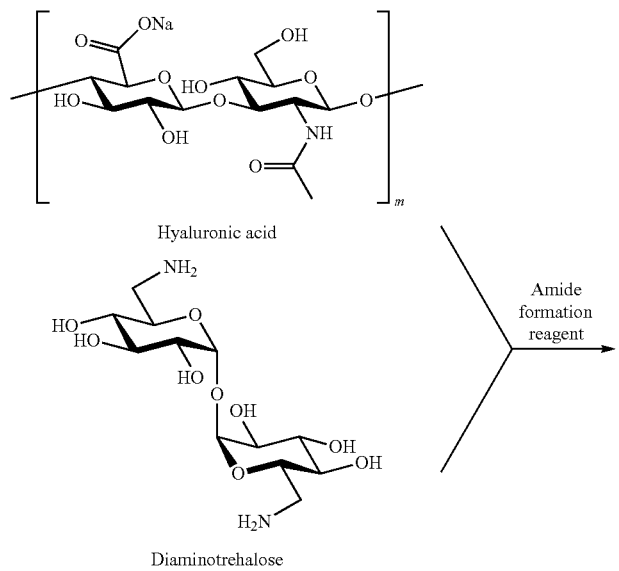
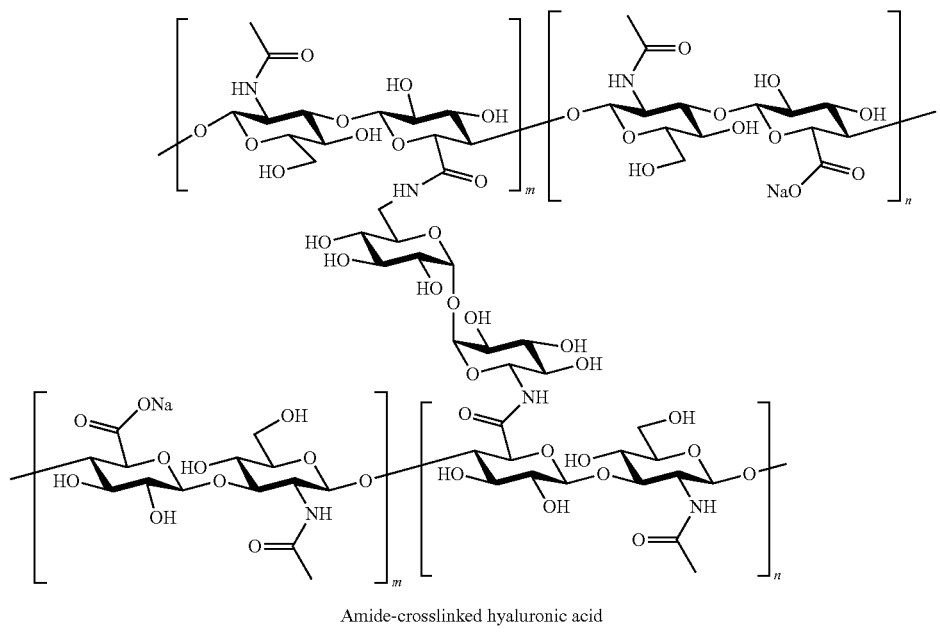
Amide-crosslinked hyaluronic acid Hyaluronic acid was weighed in a reaction vessel. A stock solution of the crosslinker (DATH) was prepared by dissolving it in buffer pH 7. DMTMM was weighed in a PTFE-container and the crosslinker-solution was added to the DMTMM to dissolve it. The pH of the DMTMM-crosslinker solution was adjusted to 6-7 with 1.2 M HCl and then added to the HA. The contents was thoroughly homogenized and then incubated at 23° C. for 24 h. The resulting material was pressed through a 1 mm steel mesh two times, swelled in 0.9% NaCl and the pH adjusted to 7.3-7.5 with diluted acid/base. The gel was subjected to heat (70° C., 24 h) in order to hydrolyze any potential ester bonds. The gel was particle size reduced through a 125 μm mesh followed by precipitation with ethanol and the precipitate was washed with 100 mM NaCl in ethanol (70% w/w) to remove excess reagents and then with ethanol (70% w/w) to remove salts and finally with ethanol to remove water. The precipitate was then dried in vacuum over night. The gels were swelled in phosphate saline buffer to 20 mg/mL HA, filled on syringes and sterilized at ($F_0$ 20). Reaction conditions and gel properties is provided in Table 3.

TABLE 3

| | | Reaction conditions | | | Results | |
|---|---|---|---|---|---|---|
| Example | <Mw> (k) | [HA] (w/w %) | DMTMM/ diHA (mol %) | DATH/ diHA (mol %) | GelP (%) | SwCC (mL/g) |
| 3-1 | 240 | 15.0 | 4.9 | 0.6 | 89 | 64 |
| 3-2 | 170 | 7.5 | 7.7 | 0.9 | 85 | 166 |
| 3-3 | 170 | 7.5 | 5.1 | 0.6 | 61 | 443 |
| 3-4 | 240 | 15.0 | 4.9 | 0.6 | 89 | 63 |

Example 3b—Comparative Example, Two Step Process for Manufacturing of Amide Crosslinked Hyaluronan Gels Grafted with Dextran; Step 2

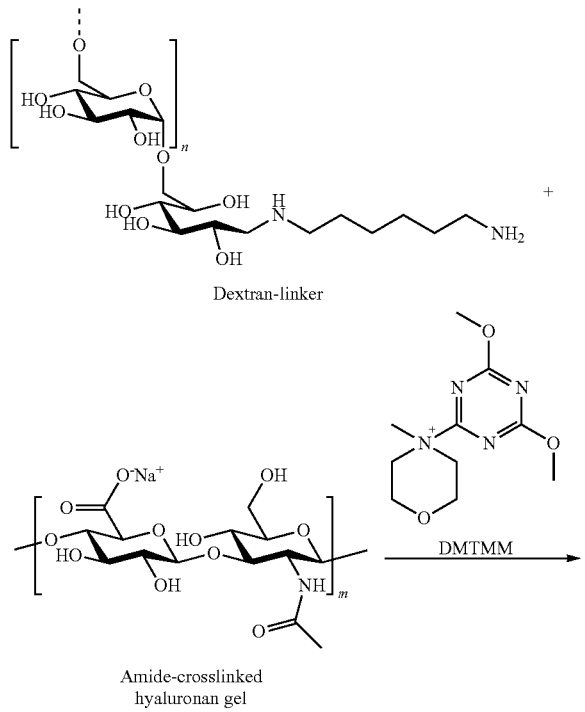

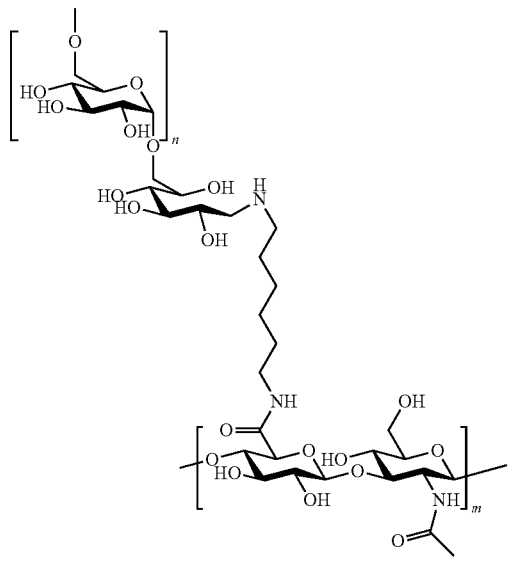

Dextran grafted to amide-crosslinked hyaluronan gel

Dextran functionalized with hexamethylenediamine according to Example 1 was grafted to hyaluronic acid hydrogels from Example 3-1 to 3-4. A general manufacturing procedure is described below.

Dextran modified at the reducing end with hexamethylenediamine (from Example 1) and DMTMM were weighed in a glass or PTFE bottle. 1 mM phosphate buffer pH 7.4 was added to dissolve the reagents. Precipitated hyaluronan hydrogel (from Example 3a) was added to the reaction solution while stirring so that a concentration of 20 mg/mL hyaluronan was obtained. The sample was incubated at 50° C. or stirred at ambient temperature for approx. 24 hrs.

The reaction was stopped by increasing the pH to 13.0 with 0.25 M NaOH, and after stirring for 60-90 min the mixture was neutralized with diluted HCl to neutral pH. The gel was purified by continuously washing with 0.9% NaCl and then precipitated by slowly adding ethanol up to 70% ethanol or only precipitated by slowly adding ethanol up to 70% ethanol. The precipitate was washed with 70% ethanol. The precipitated gel powder was subsequently washed with ethanol and dried under vacuum. The gel powder was swelled in phosphate saline buffer to 20 mg/mL HA and filled on syringes. and sterilized ($F_0$ 20). A short summary of the. Summary of reaction conditions and gel properties are presented in Table 4.

TABLE 4

| Example | Reaction conditions | | | Results | | | |
|---|---|---|---|---|---|---|---|
| | Gel used from example | Eq DEX-amine/diHA | Eq DMTMM/diHA | MoD (DEX/diHA) (%) | GelP (%) | [PS] (mg/mL) | SwCC (mL/g) |
| 3-5 | 3-1 | 0.41 | 5 | 30 | 97 | 60 | 29 |
| 3-6 | 3-1 | 0.41 | 1.25 | 26 | 96 | 59 | 43 |
| 3-7 | 3-2 | 0.41 | 5 | 26 | 95 | 44 | 56 |
| 3-8 | 3-2 | 0.41 | 1.25 | 27 | 94 | 27 | 88 |
| 3-9 | 3-3 | 0.41 | 5 | 28 | 96 | 42 | 94 |
| 3-10 | 3-3 | 0.41 | 1.25 | 20 | 97 | 33 | 191 |
| 3-11 | 3-4 | 0.30 | 5 | 18 | 97 | 79 | N.A |
| 3-12 | 3-4 | 0.30 | 1.25 | 17 | 96 | 68 | N.A |

Eq = mol(X)/mol(Y),
PS = polysaccharide (DEX + HA)

Example 4a—Comparative Example; Simulation Showing the Apparent Mw for HA in Gels for One-Pot Process for Manufacturing of Amide Crosslinked Hyaluronan Gels Grafted with Dextran Hyaluronic acid (HA, Mw 260 k) was weighed in a reaction vessel. DMTMM was dissolving it in 1 mM phosphate buffer, the pH measured and, if needed adjusted, to pH 7. The DMTMM-solution was added to the pre-weighted (for details, see Table 5, step 1) HA. The mixture was thoroughly homogenized and then incubated at 50° C. for 24 h. The resulting mixture was pressed through a 1 mm steel mesh two times and then treated with NaOH solution (pH 13 for 60 min). The solution was neutralized with HCl (aq. 1.2 M) to pH 7. The polysaccharide was precipitated with ethanol. The resulting precipitate was washed with ethanol (70 w/w %) to remove salts and subsequent ethanol to remove water. The obtained powder was dried in under vacuum over night. The obtained powder was dissolved in 1 mM phosphate buffer with 0.9% NaCl and the Mw was determined by SEC-UV.

Example 4b—Comparative Example; Simulation Showing the Apparent Mw for HA in Gels for the Two Step Process for Manufacturing of Amide Crosslinked Hyaluronan Gels Grafted with Dextran Hyaluronic acid (HA, Mw 260 k) was weighed in a reaction vessel. DMTMM was dissolving it in 1 mM phosphate buffer, the pH measured and, if needed adjusted, to pH 7. The DMTMM-solution was added to the pre-weighted (for details, see Table 5, step 1) HA. The mixture was thoroughly homogenized and then incubated at 23° C. for 24 h. The resulting mixture was pressed through a 1 mm steel mesh two times and then treated with NaOH solution (pH 13 for 60 min). The solution was neutralized with HCl (aq. 1.2 M) to pH 7. The polysaccharide was precipitated with ethanol. The resulting precipitate was washed with ethanol (70 w/w %) to remove salts and subsequent ethanol to remove water. The obtained powder was dried in under vacuum over night.

The obtained power was weighed in a reaction vessel. DMTMM was dissolving it in 1 mM phosphate buffer, the pH measured and, if needed adjusted, to pH 7. The DMTMM-solution was added to the pre-weighted (for details, see Table 5, step 2) HA. The mixture was thoroughly homogenized and then incubated at 50° C. for 24 h. The resulting mixture was pressed through a 1 mm steel mesh two times and then treated with NaOH solution (pH 13 for 60 min). The solution was neutralized with HCl (aq. 1.2 M) to pH 7. The polysaccharide was precipitated with ethanol. The resulting precipitate was washed with ethanol (70 w/w %) to remove salts and subsequent ethanol to remove water. The obtained powder was dried in under vacuum over night. The obtained powder was dissolved in 1 mM phosphate buffer with 0.9% NaCl and the Mw was determined by SEC-UV.

As seen in Table 5, the Mw after the process described in both 4a and 4b shows that the reduction in Mw correlate independently of the one-pot or two step process is applied.

TABLE 5

| | Reaction Conditions | | | | |
|---|---|---|---|---|---|
| Example | HA Start <Mw> (k) | DMTMM/ HA (mol %) step 1 | DMTMM/ HA (mol %) step 2 | HA (w/w %) | HA End <Mw> (k) |
| 4a | 260 | 125 | N.A | 15.0 | 110 |
| 4b | 260 | 4.9 | 125 | 15.0 | 110 |

Conclusion from Example 2 & 3

As can be seen in Table 6, by applying the efficient one-pot process amide crosslinked hyaluronan hydrogels grafted with dextran with properties comparable with the two step procedure can be obtained. This is also seen in Table 5.

TABLE 6

| | Reaction Conditions | | | | | |
|---|---|---|---|---|---|---|
| Example | HA Start <Mw> (k) | DATH/ HA (mol %) | DMTMM/ HA (mol %) | DEX-HMDA (mol %) | HA (w/w %) | MoD (DEX/diHA) (%) |
| 2-1 | 240 | 0.6 | 125 | 41 | 15.0 | 20 |
| 3-1 & 3-6 | 240 | 0.6 | 4.9/125 | 41 | 15.0 | 26 |
| 2-2 | 170 | 0.9 | 125 | 41 | 7.5 | 17 |
| 3-2 & 3-8 | 170 | 0.9 | 7.7/125 | 41 | 7.5 | 27 |
| 2-3 | 170 | 0.6 | 125 | 41 | 7.5 | 20 |
| 3-3 & 3-10 | 170 | 0.6 | 5.1/125 | 41 | 7.5 | 20 |

The invention claimed is:
1. A method of preparing a hydrogel product comprising crosslinked glycosaminoglycan molecules, the method comprising:
   (a) providing a mixed solution comprising glycosaminoglycan molecules, a di- or multinucleophilic functional crosslinker, and a mononucleophilic functional graft chain;

(b) activating carboxyl groups on the glycosaminoglycan molecules with a coupling agent to form activated glycosaminoglycan molecules; and (c) simultaneously crosslinking the activated glycosaminoglycan molecules with the crosslinker and grafting the graft chain to the activated glycosaminoglycan molecules by reacting nucleophilic groups of the crosslinker and the graft chain with the activated carboxyl groups, wherein the coupling agent and free crosslinker are simultaneously present at a concentration ratio of about 125/0.6 to about 125/0.9.

2. The method according to claim 1, wherein the glycosaminoglycan molecules are selected from the group consisting of hyaluronic acid, chondroitin, and chondroitin sulfate, and mixtures thereof.

3. The method according to claim 1, wherein the crosslinker comprises a spacer group selected from the group consisting of di-, tri-, tetra-, and oligosaccharides.

4. The method according to claim 1, wherein the nucleophilic groups of the crosslinker are selected from the group consisting of primary amine, hydrazine, hydrazide, carbazate, semi-carbazide, thiosemicarbazide, thiocarbazate, and aminoxy.

5. The method according to claim 4, wherein the nucleophilic groups of the crosslinker are primary amine.

6. The method according to claim 1, wherein the crosslinker is a dinucleophilic functional crosslinker.

7. The method according to claim 6, wherein the crosslinker is selected from the group consisting of diamino hyaluronic acid tetrasaccharide, diamino hyaluronic acid hexasaccharide, diamino trehalose, diamino lactose, diamino maltose, diamino sucrose, chitobiose, and diamino raffinose.

8. The method according to claim 5, wherein the crosslinker is an at least partially deacetylated hyaluronic acid.

9. The method according to claim 1, wherein the crosslinking and grafting of step (c) provides amide bonds between glycosaminoglycan molecules and crosslinkers and between glycosaminoglycan molecules and graft chains.

10. The method according to claim 1, wherein the mononucleophilic functional graft chain is a mononucleophilic functional carbohydrate.

11. The method according to claim 1, wherein the mononucleophilic functional graft chain is an aminodextran and/or an aminocyclodextrin.

12. The method according to claim 11, wherein the molar ratio of the aminodextran and/or aminocyclodextrin to disaccharide repeating units of the glycosaminoglycan is 0.1-50%.

13. The method according to claim 11, wherein the aminodextran and/or aminocyclodextrin contain a linking group having an amino group, and wherein the linking group of the aminodextran and/or aminocyclodextrin forms an amide bond with an activated carboxyl group of the glycosaminoglycan.

14. The method according to claim 13, wherein the linking group comprises a C1-6 alkyl.

15. The method according to claim 11, wherein the aminodextran and/or aminocyclodextrin is an aminodextran.

16. The method according to claim 15, wherein the aminodextran has an average molecular weight of less than 10 kDa.

17. The method according to claim 16, wherein the aminodextran is covalently grafted to the activated glycosaminoglycan by single end-point attachment.

18. The method according to claim 15, wherein the aminodextran is functionalized at the reducing end with a diamine.

19. The method according to claim 11, wherein the aminodextran and/or aminocyclodextrin is an aminocyclodextrin.

20. The method according to claim 19, wherein the aminocyclodextrin is constituted by 5-32 glucopyranoside units.

21. The method according to claim 20, wherein the aminocyclodextrin is constituted by 6 glucopyranoside units (α-cyclodextrin).

22. The method according to claim 20, wherein the aminocyclodextrin is constituted by 7 glucopyranoside units (β-cyclodextrin).

23. The method according to claim 20, wherein the aminocyclodextrin is constituted by 8 glucopyranoside units (γ-cyclodextrin).

24. The method according to claim 20, wherein the aminocyclodextrin is 6-aminocyclodextrin.

25. The method according to claim 1, wherein at least 90% of the bonds between glycosaminoglycan molecules and crosslinkers and between glycosaminoglycan molecules and graft chains are amide bonds.

26. The method according to claim 1, wherein less than 5% of the bonds between glycosaminoglycan molecules and crosslinkers and between glycosaminoglycan molecules and graft chains are ester bonds.

27. The method according to claim 1, wherein the coupling agent is DMTMM.

28. The method according to claim 27, wherein a ratio of the DMTMM to disaccharide repeating units of the glycosaminoglycan is in the range of 1-3.

29. The method according to claim 27, wherein a ratio of the DMTMM to disaccharide repeating units of the glycosaminoglycan is in the range of 3-8.

* * * * *